(12) United States Patent
Florent et al.

(10) Patent No.: US 10,157,491 B2
(45) Date of Patent: Dec. 18, 2018

(54) REAL-TIME SCENE-MODELING COMBINING 3D ULTRASOUND AND 2D X-RAY IMAGERY

(71) Applicant: KONINKLIJKE PHILIPS N.V., Eindhoven (NL)

(72) Inventors: Raoul Florent, Ville D'Avray (FR); Olivier Pierre Nempont, Suresnes (FR); Pascal Yves Francois Cathier, Asnières-sur-Seine (FR); Niels Nijhof, Utrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 572 days.

(21) Appl. No.: 14/649,225

(22) PCT Filed: Dec. 24, 2013

(86) PCT No.: PCT/IB2013/061307
§ 371 (c)(1),
(2) Date: Jun. 3, 2015

(87) PCT Pub. No.: WO2014/102718
PCT Pub. Date: Jul. 3, 2014

(65) Prior Publication Data
US 2015/0302634 A1    Oct. 22, 2015

(30) Foreign Application Priority Data
Dec. 28, 2012 (EP) ..................................... 12306698

(51) Int. Cl.
*A61B 6/00* (2006.01)
*A61B 8/00* (2006.01)
(Continued)

(52) U.S. Cl.
CPC ............ *G06T 15/205* (2013.01); *A61B 6/487* (2013.01); *A61B 6/5247* (2013.01); *A61B 8/483* (2013.01); *A61B 8/5261* (2013.01); *G06T 3/40* (2013.01); *G06T 7/30* (2017.01); *G06T 15/20* (2013.01); *A61B 6/4441* (2013.01); *A61B 6/461* (2013.01); *A61B 6/503* (2013.01); *A61B 8/0883* (2013.01); *A61B 8/12* (2013.01); *A61B 8/466* (2013.01);
(Continued)

(58) Field of Classification Search
None
See application file for complete search history.

(56) References Cited

U.S. PATENT DOCUMENTS 6,102,866 A    8/2000  Nields et al.
6,208,883 B1   3/2001  Holupka et al.
(Continued)

FOREIGN PATENT DOCUMENTS

WO    2008120136 A1    10/2008
WO    2011070492 A1    6/2011

*Primary Examiner* — Patricia Park

(57) ABSTRACT

An apparatus for visualizing image material in a multimodal imaging environment. Images (XF, USV) from an X-ray imager (100) and an ultrasound probe (USP) are fused into an interactive graphics display (GUI) to form a 3D scene, where, alongside to a 3D rendering (USS) of an ultrasound volume (USV) an X-Ray projection plan (XF) is displayed in perspective within the same scene. The rendering is according to a user selected view (UV) which is changeable upon user interaction with the interactive graphics display (GUI).

9 Claims, 5 Drawing Sheets

(51) Int. Cl.
  *G06T 7/00* (2017.01)
  *G06T 15/20* (2011.01)
  *G06T 3/40* (2006.01)
  *G06T 7/30* (2017.01)
  *A61B 8/08* (2006.01)
  *A61B 8/12* (2006.01)
  *A61B 34/00* (2016.01)
  *A61B 90/00* (2016.01)

(52) U.S. Cl.
  CPC ......... *A61B 34/25* (2016.02); *A61B 2090/364* (2016.02); *A61B 2090/376* (2016.02); *A61B 2090/3784* (2016.02); *F04C 2270/041* (2013.01); *G06T 2200/04* (2013.01); *G06T 2200/08* (2013.01); *G06T 2207/10081* (2013.01); *G06T 2207/10121* (2013.01); *G06T 2207/10136* (2013.01); *G06T 2207/20104* (2013.01); *G06T 2207/20221* (2013.01); *G06T 2207/30048* (2013.01); *G06T 2207/30204* (2013.01); *G06T 2210/41* (2013.01)

(56) References Cited

U.S. PATENT DOCUMENTS

| | | |
|---|---|---|
| 7,141,020 B2 | 11/2006 | Poland et al. |
| 7,496,398 B2 | 2/2009 | Nields et al. |
| 8,027,710 B1 | 9/2011 | Dannan |
| 8,715,189 B2 | 5/2014 | Kanayama et al. |
| 2004/0068170 A1 | 4/2004 | Wang et al. |
| 2007/0276243 A1* | 11/2007 | Gerard ............... A61B 6/12 600/440 |
| 2009/0002366 A1 | 1/2009 | Kanitsar et al. |
| 2010/0020161 A1* | 1/2010 | Bertrams ............ G06T 7/33 348/51 |
| 2011/0058653 A1* | 3/2011 | Baumgart ........... G06T 19/00 378/98.2 |
| 2011/0172531 A1 | 7/2011 | Kanayama et al. |
| 2011/0249793 A1* | 10/2011 | Lalena ............... A61B 6/46 378/62 |
| 2011/0311026 A1* | 12/2011 | Lalena ............... A61B 6/4405 378/98.5 |
| 2012/0296202 A1 | 11/2012 | Mountney et al. |
| 2015/0049862 A1* | 2/2015 | Ancar ............... A61B 6/08 378/190 |

* cited by examiner

REAL-TIME SCENE-MODELING COMBINING 3D ULTRASOUND AND 2D X-RAY IMAGERY

CROSS-REFERENCE TO PRIOR APPLICATIONS

This application is the U.S. National Phase application under 35 U.S.C. § 371 of International Application Serial No. PCT/IB2013/061307, filed on Dec. 24, 2013, which claims the benefit of EP Application Serial No. 12306698.7, filed on Dec. 28, 2012. These applications are hereby incorporated by reference herein.

FIELD OF THE INVENTION

The invention relates to an apparatus for visualizing image material in a multimodal imaging environment, to a method of visualizing image material in a multimodal imaging environment, to an imaging system, to a computer readable medium, and to a computer program product.

BACKGROUND OF THE INVENTION

One of the challenges of image-guided medical, in particular surgical, procedures is to efficiently use the information provided by the many imaging techniques the patient may have been through before and during the intervention.

For example, in cardiology, physicians often have access to real-time X-ray images acquired by a C-arm. These images have a very good spatial and temporal accuracy thus enabling to follow precisely the progression of even thin catheters and other interventional tools. However, soft-tissues are barely visible in these images, and furthermore, these images are projections which do not give a direct access to the volumetric geometry of the intervention scene. To gain access to this important information also, a solution consists in using a second imaging modality which is both 3D and able to image soft-tissues.

One possible choice for this second imaging system is 3D ultrasound imaging. The advantage of this modality is that it can be used in real-time during the surgical procedure. In cardiological procedure, trans-esophageal probes can be navigated right next to the heart, producing real-time volumetric images with anatomical details that are hardly visible with standard transthoracic ultrasound.

A typical intervention is percutaneous valve repair (PVR) such as mitral clipping where the simultaneous involvement of X-ray and ultrasound has been found helpful to monitor the placement of the tool/endoprosthesis with respect to the soft-tissue anatomy.

It has been found however that the the usual way of displaying both ultrasound and X-ray real-time streams, such as in Applicant's US WO 2011/070492, are at times not intuitive enough for the operator to readily understand the spatial relationship between the two modalities when carrying out the intervention, oftentimes under great stress.

SUMMARY OF THE INVENTION

There may therefore be a need for an alternative system for visualization of both, an ultrasound and an X-ray image.

The object of the present invention is solved by the subject matter of the independent claims where further embodiments are incorporated in the dependent claims. It should be noted that the following described aspect of the invention equally applies to the method of visualizing image material in a multimodal imaging environment, to the imaging system, to the computer program element and to the computer readable medium.

According to a first aspect of the invention there is provided an apparatus for visualizing image material in a multimodal imaging environment.

The apparatus comprises:

an input port for receiving i) an ultrasound image data set acquired of an object by an ultrasound probe and, ii) an X-ray image of the object acquired by an X-ray imager detector in a plane at a projection direction through exposure of the object to radiation emanating from the X-ray imager's X-ray source;

a registration unit configured to register the ultrasound image data set in a common coordinate frame for both, the X-ray imager and the ultrasound probe;

a graphics display generator configured to generate on a screen a graphics display of a 3D scene at a user selectable view that affords, in the common coordinate frame for both, the X-ray imager and the ultrasound probe, a representation of i) a 3D projection of the ultrasound image data set(at the user selectable view), and ii) a perspective 3D view on the X-ray image in the detector plane, said perspective 3D view corresponding to the X-ray projection direction (defined, for example, by a position in space of X-ray imager's X-ray source) and the user selected view, the generator configured to update the 3D scene according and in response to a user selected second view on the 3D scene.

In other words, according to one embodiment, the apparatus operates to effect a modeling of the 3D scene that is based on the two images, the ultrasound image data set and the x-ray frame, and on geometrical information corresponding to both acquisition means, and to a registration transform computed from the pair of images that spatially "links" both acquisition means. This results in the graphics display affording to the human observer a single and natural glimpse of the spatial relationship between the two modalities.

The apparatus operates very much unlike previous multimodal image viewers, where the images are merely shown in a multi-pane window, one pane for each modality so that the spatial relationship between the imaging modalities would not present itself naturally to the user.

The user selected view can be thought of as a "camera" in 3D space that operates to capture the combined scene formed by the two imaging modalities in 3D space. The view is defined by i) a position in the common frame of reference, ii) a viewing direction with a viewing orientation, and iii) a solid angle extending from said position along said direction. The second view may result from the previous view through modifications such as translation, rotation or (de-)magnification or a combination of those modifications as requested by the user. The user selected view on the 3D scene affords said view in particular on the ultrasound image data set and the x-ray frame in its plane.

According to one embodiment the generator is configured to generate, responsive to a de-magnification request, a zoomed-out version of the 3D scene so as to accommodate a length of the imager's SID (Source to Image-receptor Distance) in that version of the 3D scene, with a visual marker indicating a position of the X-ray source relative to the X-ray image in the detector plane at the user selected view on the 3D scene, in particular on the X-ray frame in its plane and on the ultrasound volume.

In other words, upon choosing the right scaling, the combined scene is modeled into the graphics display, so includes the X-ray source position, the 3D rendering of the ultrasound image set under the selected view, and the corresponding X-ray plane, seen in perspective, on which plane the 2D X-ray image is projected and possibly warped because of perspective distortion. The user can visually grasp at once the overall arrangement in 3D space of the two modalities with their respective imaging geometry.

According to one embodiment the generator is configured to generate, responsive to a user designating a point of interest in the X-ray image, a line of sight extending from said point of interest across the ultrasound image data in the selected view on the 3D scene and extending to the position of the X-ray source. The generator is operative to generate a marker to visually designate a corresponding point on the line and where said line intersects the ultrasound image data in the selected view on the 3D scene.

According to one embodiment the generator is configured to generate, responsive to a user designating a point of interest in the ultrasound image data set in the selected view on the 3D scene, a line of sight extending from said point of interest to the position of the X-ray source and extending to a corresponding point in the X-ray image and on the line where said line interests the X-ray image. The generator is operative to generate a marker to visually designate the corresponding point in the X-ray image.

Said lines of sight arise geometrically by connecting the location of the X-ray source with the point in the X-ray image (representative of the detector plane) that is the projection (according to a current X-ray acquisition geometry) of the point in the ultrasound image data.

In one embodiment, the apparatus affords the further functionality of allowing the user to manually adjust the position the marker along the line and in the ultrasound image data set. In one embodiment, an automatic adjustment algorithm is used instead based on the similarity of image contents (in the X-ray image and the ultrasound image data) in respective neighborhoods of the respective markers.

Anatomical landmarks or medical devices (catheter or guide-wires) can be so designated by the user and then tracked in one or two modalities, with the line of sight naturally linking both designations of the same object/point within the 3D scene. The points of interest may also be automatically detected by statistical inference.

According to one embodiment the ultrasound image is one in a stream of ultrasound image data sets and wherein the X-ray image is one in a stream of X-ray images, the two image streams registered in the common frame of reference, the generator comprising a tracker to track the point of interest over time in the X-ray image stream or in the ultrasound image data set stream, the generator configured to re-generate the corresponding point in the selected view on the respective ultrasound image data set in the stream or in the respective X-ray image in the stream, and to adapt the line of sight in responsive to a change in position of the X-ray source or of the ultrasound probe.

According to one embodiment the graphics display is an interactive one and is configured to receive the user selected first or second view or the de-magnification request. In particular and according to one embodiment the screen is a touch-screen and the user selection of the view including de-magnification request is by a manual touch or swipe action on the screen. According to another embodiment the user selection of the view including the de-magnification request is by actuating a key on a keyboard or by actuating a pointer tool, the keyboard or the pointer tool communicatively coupled to the apparatus.

The ultrasound image data set as envisaged herein is acquired by a 3D ultrasound equipment so forms a 3D image volume. However the apparatus may also be used with a 2D ultrasound imager where a sequence of 2D slices is produced instead. The 3D scene is then formed by fusing the two 2D images (the X-ray projection image and the 2D ultrasound slice) in their respective image planes into a 3D perspective view with possibly one or both of the 2D images warped due to perspective distortion.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
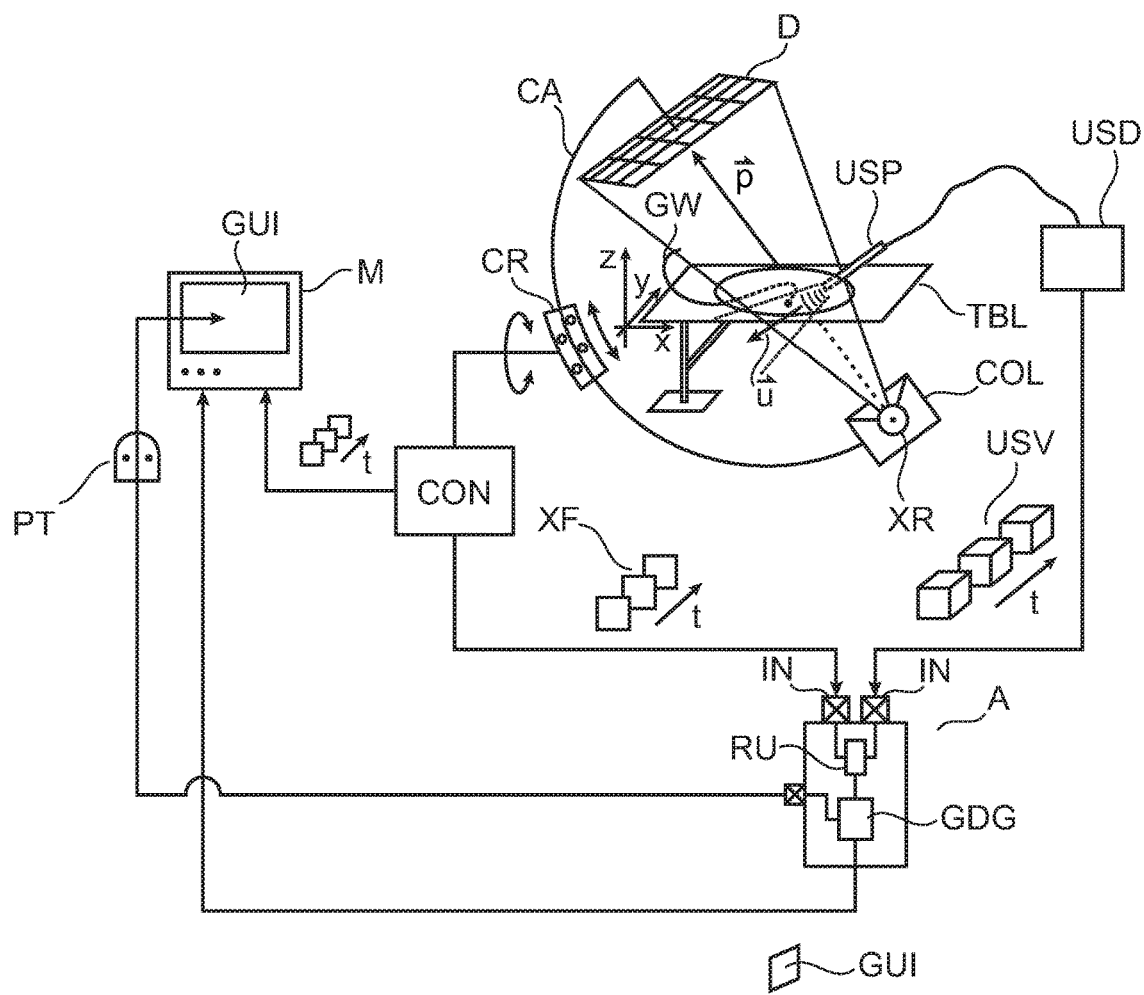
FIG. 1 shows a multimodal imaging arrangement for image-guided support of an intervention.

With reference to FIG. 1 there is shown an arrangement for multimodal image-guided support of minimal invasive interventions such as mitral clipping.

Broadly, said arrangement comprises an X-ray imager 100, an examination table TBL and ultrasound imaging equipment USD. Specifically, the arrangement allows acquiring images from both, the ultrasound imager and the X-ray imager. As will be explained below in more detail, the two image streams are combined in a manner so as to harness as user desired the most suitably one of the two streams for relevant anatomic information.

During the intervention a patient PAT is disposed on examination table TBL. A medical device such as a guide-wire GW is introduced through an entry point into the patient's body and the interventional radiologist faces the challenge of navigating said guide-wire through the complex maze of patient's vasculature to arrive at a lesioned site. An example for such an intervention that relies on multimodal imaging support is mitral valve clipping, a cardiac intervention. The guidewire GW is threaded by the interventional radiologist ("operator") through the cardiac vasculature from an entry point (eg, patient's PAT femoral vein) all the way up to the mitral valve. A clip is fed through the catheter to grasp and to tighten the valves' leaflets to so prevent blood from leaking. In mitral valve clipping it is therefore imperative to not only know the position or location of the catheter/guidewire GE tip but also the position of the valve's leaflet as it oscillates during cardiac activity. This is where the multimodality comes into play: whereas the X-ray fluoroscopic images are capable of recording the guidewire or "footprint" (image portion representative of the projection view) thanks to the guidewire/guide catheters GW's radiation opacity, the cardiac soft tissue (such as the valve leaflet) is only visible in the ultrasound image but not (or barely so) in the X-ray image for lack of such radiation opacity.

The X-ray imager is of the C-arm type and allows acquiring X-ray projection images from the patient at the region of interest at different projection directions p. However imager constructions other than C-arm are also envisaged herein. As indicated in FIG. 1, the imaging geometry such as the position of the C-arm CA can be changed relative to the patient to so effect the different projection directions p. In the embodiment, C-arm CA carries at one of its ends a detector D and at the other, opposing, end a collimator X-ray tube assembly. The imaginary line of sight extending between the X-ray tube XR and the detector will be referred to herein as the "SID line" whose length is an imaging parameter often referred to as the SID (Source to Image-receptor Distance).

The collimator COL collimates X-ray beam as emitted by X-ray source XR. The C-arm CA is rotatable around its center by sliding in clockwise or counterclockwise orientation in a cradle CR having a suitable ball-bearing and a rail arrangement. In other embodiments, the imager's geometry enjoys more degrees of freedom. For example, the entire c-arm CA is shiftable in a plane X,Y defined by the table TBL's edges. This can be achieved by an overhead carriage that is slidable in X,Y direction and that includes a suspension arm that carries cradle CR and C-arm CA. Overall control of the operation of the X-ray imager is via a console CON that provides manual control means such as pedal or joystick or that can be programmed to run a protocol for the acquisition of an X-ray image stream) $XF_t$.

Ultrasound imaging equipment USD includes an ultrasound probe USP that is positionable in any desired position or orientation u relative to patient PAT. In one embodiment, the probe USP is introduced into the patient PAT. The probe USP is configured to transmit ultrasound pulse waves which are bouncing off structures in the patient's anatomy. The probe is further configured to register the bounced off waves as incoming echo sound waves and a processor in the equipment calculates the travel time of said incoming echo waves to form a 3D ultrasound image data volume at the instant propagation direction u at a specific time instant t. During the intervention, the propagation direction u is likely to change a number of times so that ultrasound equipment USD outputs a sequence of 3D volumes $USV_t$. An example of a 3D ultrasound equipment is Applicant's U.S. Pat. No. 7,141,020.

The two image data streams, that is, the fluoroscopic X-ray image frames XF ("fluoros") and the ultrasound volumes USV, are then forwarded to an apparatus A to image-process said images or sequence of images to form a graphical user interface GUI which is then rendered for view on a screen M. Operation of apparatus A will be described in more detail below.

The propagation direction u and the projection direction p are part of the ultrasound or X-ray imaging geometry, respectively. Both geometries can be spatially related to each other (and to patient PAT) by a common frame of reference X,Y,Z. As can be seen in FIG. 1, an example of a common frame of reference is defined by the plane X,Y of the examination table TBL and a direction z that is perpendicular to said plane. However it will be understood by those schooled in the art, that other definitions for a common frame of reference for both modalities can likewise be employed in the present teaching.

Figure 2:
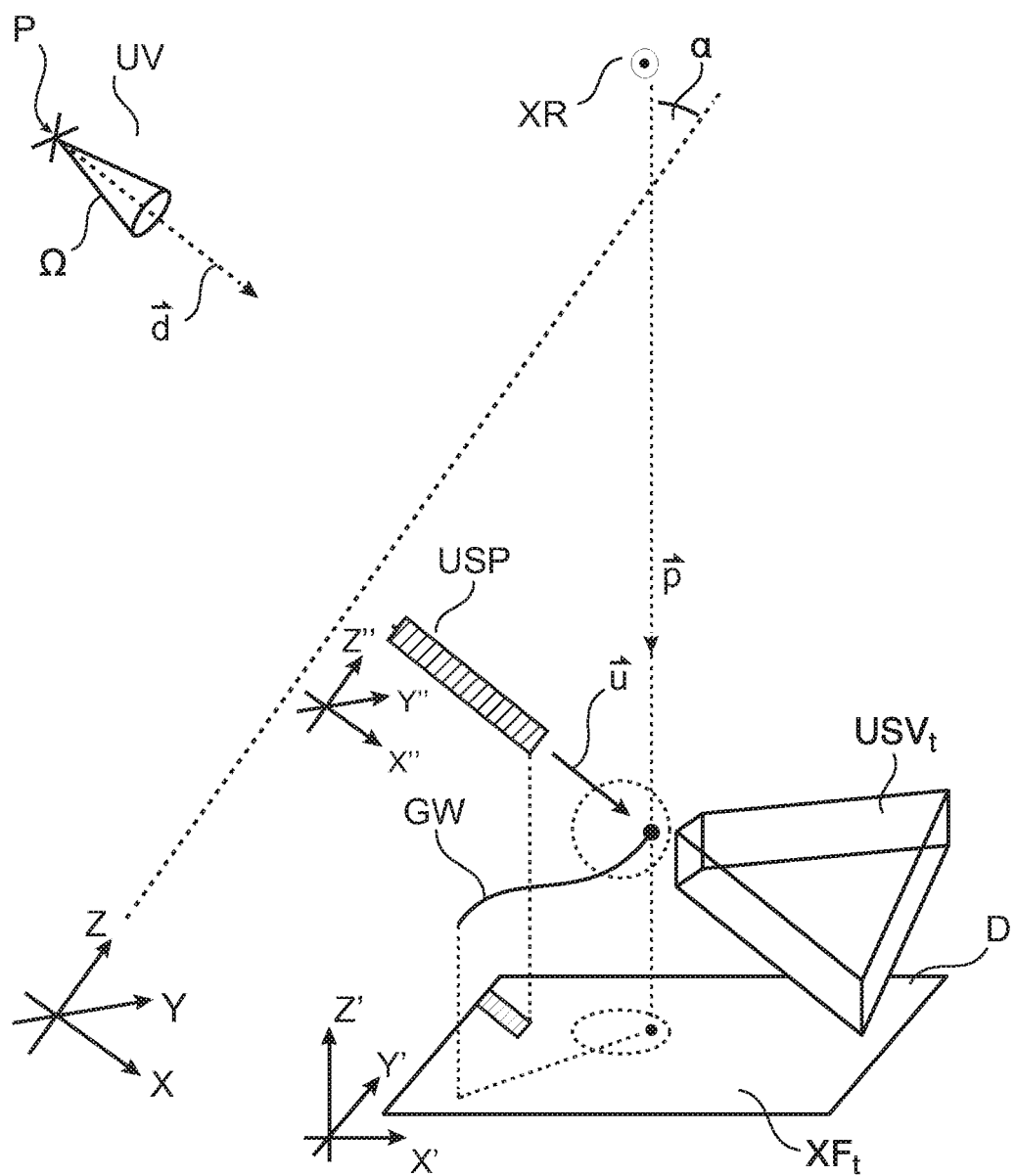
FIG. 2 is a schematic close-up of the imaging geometry in the arrangement of FIG. 1.

With reference to FIG. 2, a more detailed view of the three-dimensional geometry in respect of the imaging modalities is shown.

The depiction of the situation in FIG. 2 is to be understood as a snapshot at a certain time instant t. At said time instant t, guidewire GW is at a certain position which can be defined by the positioning in space of guide-wire's tip TP. A relatively small area round said tip defines a neighborhood as indicated in the Figure by the area inside the dashed circle. In other words, a position of the guidewire GW's tip TP at a time instant t defines an instantaneous region of interest ROI that changes as the guidewire GW is made to advance or made to "curl" during the course of the intervention.

At time instant t an X-ray frame XF (of stream $XF_t$) is acquired as shown in FIG. 2 at projection direction p. In other words, an X-ray beam passes through said instantaneous region of interest and forms an image in the detector plane D which is then recorded by detector cells as the fluoroscopic X-ray frame XF at said time instant t. The detector cells are arranged in a local co-ordinate system defined by the detector D surface plane indicated in FIG. 2 by X', Y'. As shown in FIG. 2 and owing to, in general, an oblique position of the C-arm CA, the detector D's image plane X',Y',Z' is rotated relative to the common reference frame defined by the table TBL plane X,Y,Z and the two frames of reference are related via an orthogonal transformation. An instantaneous field of view of ultrasound of probe USP has in general a frusto-conical shape as indicated in FIG. 2. In other words, the frusto-conic volume is the volume insonified, at time instant t, by the probe when placed in propagation direction u. The local frame of reference of the ultrasound probe USP acquisition geometry is shown as X", Y", Z". The US equipment USD as envisaged herein allows acquiring the instant 3D volume USV at direction u at a single probe position so no movement of the probe by hand or otherwise is needed for any given 3D volume USV. However, use of other, more traditional scanners are also envisaged herein where the 3D volume is reconstructed after insonification of the volume of interest from many different propagation direction that are each obtained by moving by hand or otherwise the scanner so as to sweep out the volume.

The respective local frame of reference of each imaging modality (X-ray and ultrasound) can be related by an orthogonal transformation to the common frame of reference. The spatial relationship between the imager's C-arm CA (and hence the X-ray source/detector D's plane) and the common frame of reference is known. The spatial link between the ultrasound probe USP's local frame and the local frame of reference of detector D on C-arm CA is gotten in one embodiment by a registration to thereby establish the link between ultrasound probe USP and the common frame of reference of the table's TBL plane. In other words, the orthogonal transformation is estimated in one embodiment by said registration as will be explained in more detail below.

View UV designates a "camera" or user selectable view on the combined 3D scene of the C-arm geometry (X ray source and detector plane D) and the US volume USV. The view UV is defined by a position P in space relative to the common frame (and hence defining a distance to the C-arm geometry), by a solid angle Ω specifying the width of the user's field of view, and by specifying the viewing direction d and orientation. Said viewing orientation can defined by a vector orthogonal to the viewing direction d to so define the concepts of "up"/down" or "left/right" for the view on the 3D scene Broadly, apparatus A as proposed herein operates to fuse the two image streams into a graphics display GUI to form a 3D scene that affords to the viewer perceiving the perspective relationship in 3D space between the two imaging modalities. An image of one stream acquired at an instant is registered in space along the common reference frame and so is an image of the other stream acquired at substantially the same instant so as to form a sequence of acquisition time synchronized multimodal pairs of registered images. In this manner the two streams are registered in the common frame of reference.

The overall 3D scene is then rendered based on a user request for a view UV (P, Ω, d) along a specified direction d on the 3D scene at a time instant. The US volume along view UV is then fused with the X-ray image frame XF in the stream $XF_t$ that is synchronized with the current US volume USV. In the fused image the view UV on the X-ray image is precisely the user selected view UV on the ultrasound volume USV. In other words, the detector D plane with the respective X-ray image XF will appear in general to the human viewer under perspective distortion. In yet other words, the X-ray image, usually displayed by a conventional visualizer in plan-view where it assumes a square or rectangular shape, will be displayed instead in a warped fashion so will in general appear as a trapezoid. The prospective distortion corresponds to the spatial relationship between the selected view UV on the US volume relative to the projection direction p. If the user further specifies a (de-) magnification or zoom level that affords a sufficiently broad view, the entire length of X-ray imager's SID line is displayed in 3D space with a marker indicating the position of the X-ray source XR relative to the detector plane, the later represented by the X-ray image warped due to perspective distortion.

FIGS. 3 and 4 afford schematic depictions at different user selected views UV on the 3D ultrasound volume and the X-ray image plane in different (de-)magnifications.

Figure 3A:
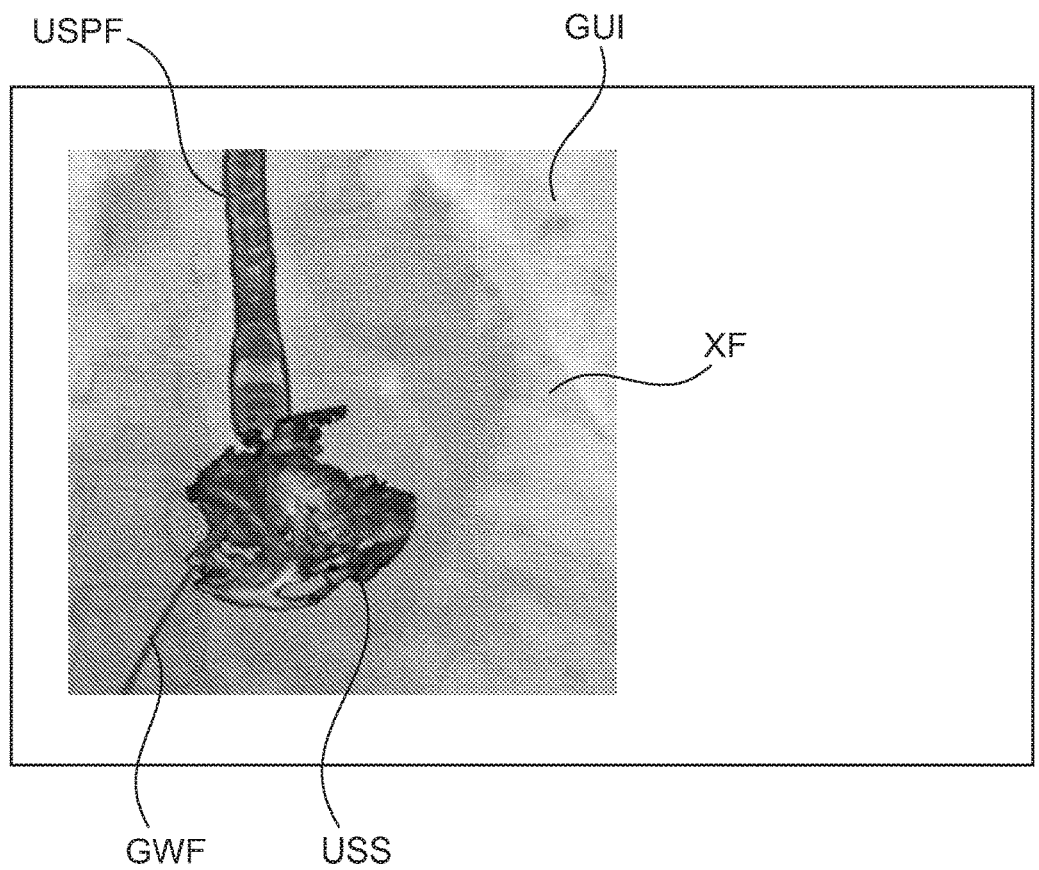
FIG. 3 is a schematic representation of a graphical user interface.

With reference to FIG. 3A there is shown a graphical user interface GUI including the fused image formed from the X-ray XF and the selected view USS on the 3D US volume USV. In FIG. 3A the direction d of the selected view direction UV (on the 3D scene, in particular on the ultrasound volume USV) is essentially aligned with the projection direction, so viewing direction d and projection direction p run essentially parallel. In other words, the 3D scene represented on the GUI confers to the user the impression as if he or she is viewing the volume USV along the imager's SID line and onto the detector plane where the X-ray image has been formed.

Figure 3B:
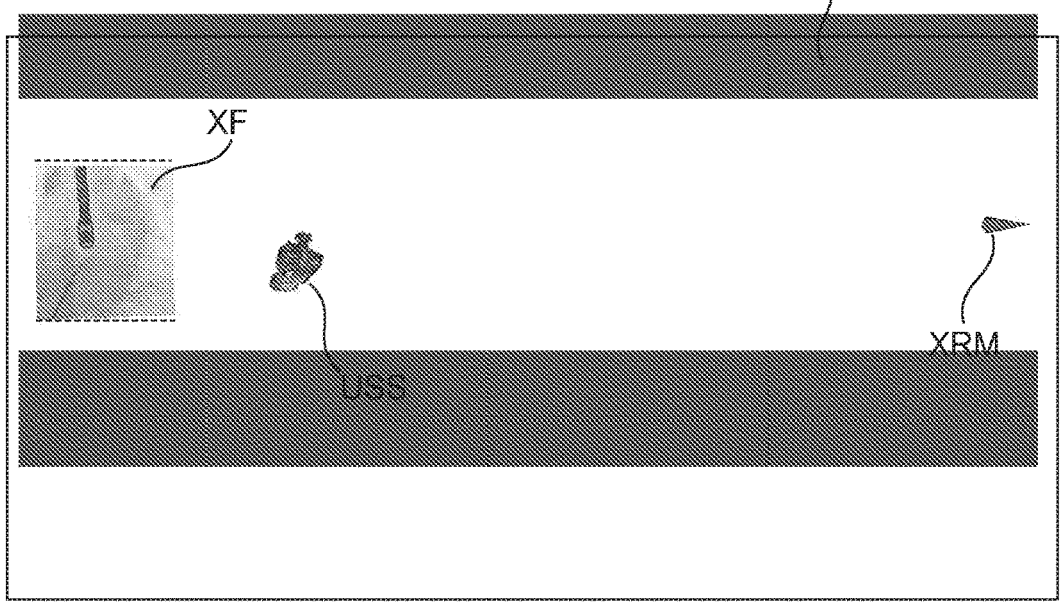

In the view UV of FIG. 3B a different viewing direction d has been chosen by the user and the user has further specified a de-magnification parameter to arrive at the view of FIG. 3B by rotation of and zooming-out from the view of as of FIG. 3A. FIG. 3A confers to the user the impression of viewing "laterally" the SID line of the imager as defined by the distance between marker XRM for the X-ray source XR and the detector image plane represented by the X-ray image XF. In one embodiment, said X-ray source marker XRM is cone-shaped. The user chosen view UV in FIG. 3B imparts a perspective distortion on X-ray image XF as evidenced by having the image plane (and with it the X-ray image XF) warped into a trapezoid. The amount of distortion is shown for clarity by the dashed lines that indicate the rectangular image area as it would appear had there been no distortion as in FIG. 3A.

In FIG. 3A, the guide-wire's footprint GWF can be seen better in the X-ray image XF but the view on the guidewire in the ultrasound image volume USV view is obstructed. This is unlike in the rotated view in FIG. 3B (see also FIG. 4B for a close-up) that now reveals the corresponding structure of the guide-wire tip in the ultrasound image volume USV also, now looked at from a different view compared to the plan view of FIG. 3A. In FIG. 3B the ultrasound volume view chosen by the viewer is roughly at 40° (measured in a reference plane) relative to the projection direction p.

Figure 4A:
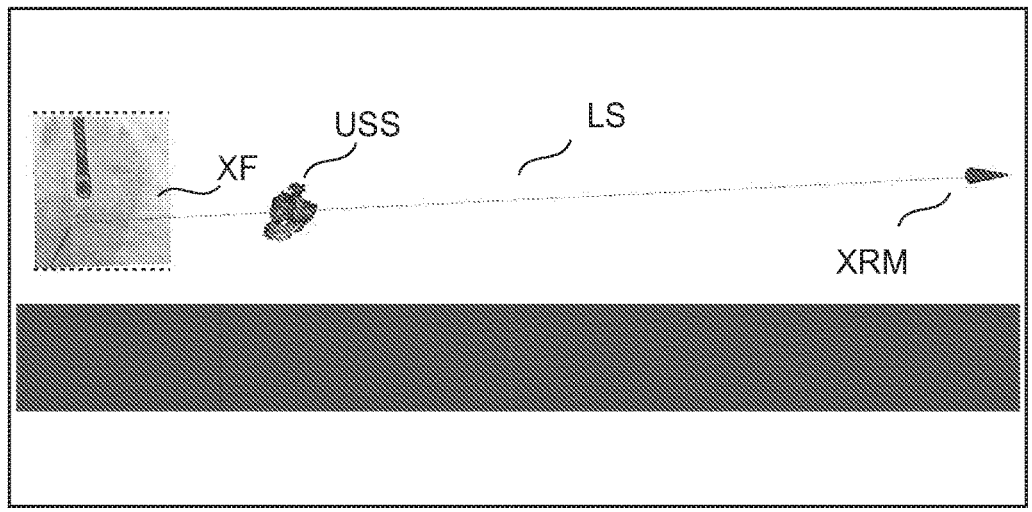
FIG. 4 is a further schematic representation of the graphical user interface.
Figure 4B:
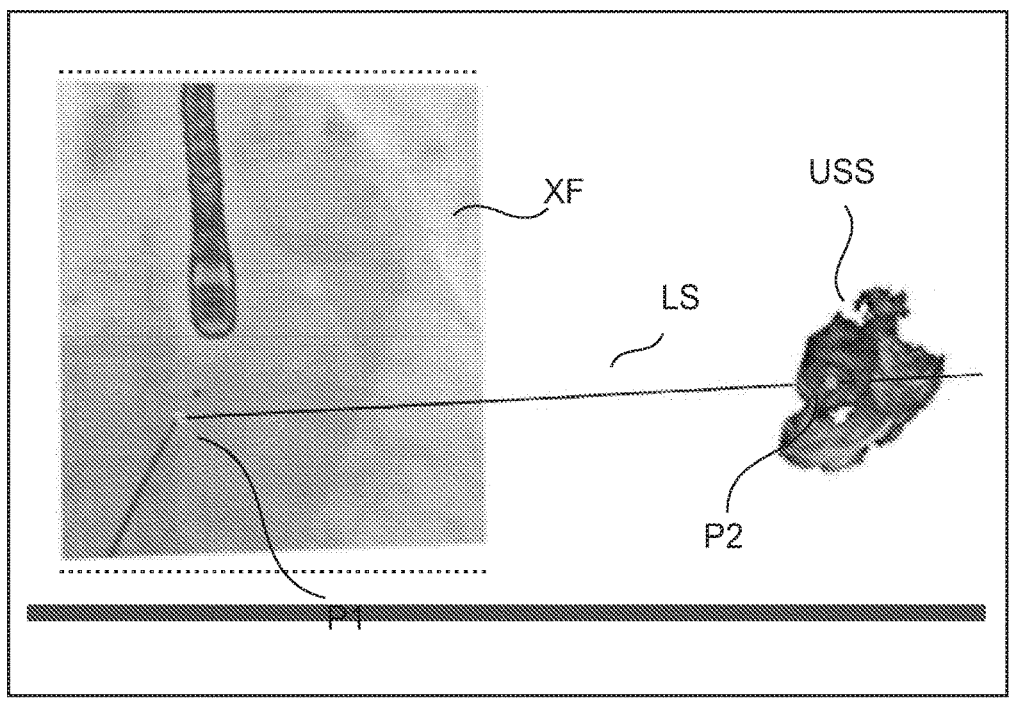

FIG. 4A is similar to FIG. 3B but now shows a correspondence line of sight LS or projection line that extends between a point P2 in the ultrasound volume USV and a spatially corresponding point P1 in the X-ray image XF plane. With further reference to FIG. 4B showing a close-up of FIG. 4A, the line of sight arises geometrically by connecting the location of the XR source with the point P1 in X-ray image plane that is the projection of the point P2 in volume USV under the instant projection direction p (that is, under the current X-ray acquisition geometry). For example, in the X-ray image the user clicks by a pointer tool PT on a current position P1 of the guide-wire's tip as indicated by the tip's footprint. Upon selection of said point, the line is rendered and emerges in the GUI to connect the selected point P1 in the XF image to a corresponding point P2 in the USV volume. That is, the pair (P1, P2) of points corresponds spatially under said projection p. Said projection line LS can also be invoked the other way around, that is, by designating, with the pointer tool, a point P2 in the ultrasound volume USV. The projection of said point in the ultrasound volume USV is then projected, by using the current acquisition geometry of the X-ray imager 100, in P1 onto the current X-ray image XF. IN this embodiment, said line LS runs through the ultrasound image and extends to the X-ray source position marker XRM.

According to one embodiment, screen M is a touch-screen and selection of said point is by touch action so users tap on the screen's surface with their finger to define the point.

FIG. 4B is obtained from the view of FIG. 4A by applying a magnification request ("zoom-in") by user input.

According to one embodiment it is envisaged that initially, a default view on the US volume is selected for example the aligned view as of FIG. 3A. The user can then change the view on the US volume as desired, e.g., as of the view in FIG. 3B.

In one embodiment, the graphics display further includes an overlay graphic element that forms a symbolic representation of the ultrasound probes USP field of view. The graphic element may be formed as a frusto-conic as shown systematically in FIG. 2 and is preferably overlaid onto the X-ray frame FX portion of the graphics display GUI.

In one embodiment, the GUI generation is in real time so the graphics display in GUI is updated at predefined time intervals as new pairs of synchronized US volumes and X-ray frames are received. IN other words the above described operation is repeated as the apparatus cycles through the said synchronized pairs in the two streams.

The line of sight LS can either be rendered dashed (FIG. 4A) or solid (FIG. 4B) or in any other desired pattern. Color coding may also be used to make the line better stand out to the eye. For example, different sections of the line may be colored differently to achieve good contrast in all parts of the graphics display.

Operation of the apparatus to produce the graphical user interfaces in FIGS. 3 and 4 is now explained in more detail.

Operation

The two streams are received at an input port IN of apparatus A. According to one embodiment there are dedicated input ports for each image stream or there is a combined image receiving port that alternates to receive either a respective X-ray frame $XF_t$ or ultrasound volume $USV_t$.

As briefly mentioned above, apparatus includes a synchronization module to synchronize the two image streams.

In other words to each X-ray frame $XF_t$ acquired at a certain time t is associated herewith an ultrasound volume $USV_t$ that is required at substantially the same time t. Synchronization of the two frames can be achieved for example by evaluating the time stamps that are attached to each X-ray image frame and each US volume USV. Each pair of so synchronized images is then spatially registered onto the common frame of reference by operation of a registration unit RU. According to one embodiment registration unit RU operates by using the footprint of the ultrasound probe in the respective X-ray frame XF and by using the geometry of the X-ray imager and the known 3D shape, of the ultrasound probe. Such a registration technique is described by Applicant's WO 2011/070492. In other words, in this embodiment registration is used to estimate the above mentioned transformation that relates the local frame of references to the common frame of reference. The registration algorithm assesses the position of the ultrasound probe USP in the local coordinate system based on the projection USPF of the probe (see FIG. 3A) in the X-ray image XF.

In other embodiments registration is not or not only image based and registration unit RU comprises a plurality of sensors (e.g., electromagnetic sensors) to assess said transformation, that is, the relative position of the imaging modalities. In one embodiment, one or more registration sensors are arranged at a-priori known positions on or around the examination table TBL or on the patient PAT to sense the position of the probe and to so provide the basis for the registration. The registration operation results in the alignment of the both, the instant x-ray frame XF and the instant ultrasound volume USV, in the common frame of reference.

The apparatus also includes an event handler (not shown) to intercept a request by the user for a desired view UV on the instant US volume USV and, by extension, on the instant X-ray frame XF in its plane. The selected view UV on the ultrasound volume USV and the X-ray frame XF that corresponds to the time stamp of the instant ultrasound volume USV is then rendered for display.

A graphics display generated GDP then fuses the two images, that is, the instant USV view and the instant X-ray frame XF, and produces a graphical user interface including said view and forwards same for display on the screen M. A graphics processor then effects and controls the displaying on the screen M.

According to one embodiment and as explained earlier in relation to FIGS. 4 and 3, said graphical user interface is interactive. In other words the graphical user interface window responds to actions executed by pointer tool PT such as a mouse or stylus or, in the case of a touch screen embodiment of screen M, by the user's finger touch carrying out touch and/or sweep action or gestures whilst contacting said screen M. For example users may move their finger across the screen to translate the current view to a new view or trace out a circle in clockwise or counterclockwise orientation to rotate the current view into a new view. In one embodiment a magnification is invoked by spreading index finger and thumb apart whilst in contact with the screen's surface to effect a zoom-in into the current 3D scene. Moving index finger and thumb the opposite way, that is, towards each other, invokes a de-magnification or zoom-out. However this is merely one embodiment and graphics display generator GDG may be programmed to interpret other suitable touch interactions to modify the current view to effect a translation, rotation or (de)-magnification.

Similar user interaction can be implemented in the mouse or stylus embodiment to change the view on the US volume by rotation, translation or de-magnification. For example, graphics display generator GDG may be programmed to interpret "click-and-drag" action to effect the change of view. For example, the user traces out circular motion in clockwise or counterclockwise orientation around the currently shown US volume. The graphics display generator responds concurrently by rendering the different views and updating the perspective view on the X-ray image XF as describe above. The translation is effect by click-and-drag along the direction of the desired translation. The different magnification or de-magnification requests can be issued by using a scroll wheel of the mouse PT. The user can then zoom in or out of the image as desired.

Setting the markers on either the X-ray or the US volume view can likewise be effected by mouse click in one embodiment. Apparatus A's event handler intercepts those mouse clicks and uses the registration information to render the line of sight to connect corresponding points in the X-ray portion and the ultrasound image portion. Invoking the line of sight LS can be effected by either clicking on the X-ray image portion or by clicking on the ultrasound image portion USS.

Although an offline mode of operation of apparatus A is also envisaged, according to a preferred embodiment apparatus A is configured to operate in real time mode. In other words, the graphical user interface as discussed herein is rendered for view as the two streams are received and is updated for each time instant throughout the respective streams. The user selected designated point in either image portion is maintained across the respective sequences and the line of sight is updated correspondingly.

In other words during operation in real time mode a line of sight will appear to move in accordance with the motion of the X-ray source XR or the ultrasound probe USV as recorded by consecutive image acquisitions in the two image streams.

According to one embodiment the point of interest can be identified automatically. For example, in one embodiment, a tip portion of guidewire GW or similar medical device that resides in the patient PAT whilst the two imaging modalities acquire their respective image streams is identified automatically across the X-ray image stream using shape and brightness priors in a Bayesian statistical inference scheme. In this way, the tip portions can be tracked across the X-ray stream and the corresponding point in the US volume view USS are likewise visually designated (by overlaying a suitable symbology such as a "cross-hair" symbol or similar or by color-coding), with the line of sight connecting the pair of points for each synchronized image pair. In other words, in this embodiment there is identification and tracking steps across each stream to identify and track anatomic landmarks or tool GW tip position. Optical flow methods may be used to achieve the tracking. When the line of sight is then invoked for those points, the line of sight will appear to the viewer to move in accordance with patient movement. Said tracking step may also be applied to manually by the user designated points of interest through pointer tool or touch action.

In sum and to put it differently, in the apparatus as proposed herein, images XF, USV from the X-ray imager 100 and the ultrasound imager USD are fused into the interactive graphics display GUI to form the 3D scene, where, alongside with the 3D rendering USS of the ultrasound volume USV, the X-ray projection plan XF is displayed in perspective within the very same 3D scene. The rendering is according to the user selected view which is changeable upon user interaction with the interactive graphics display GUI.

Figure 5:
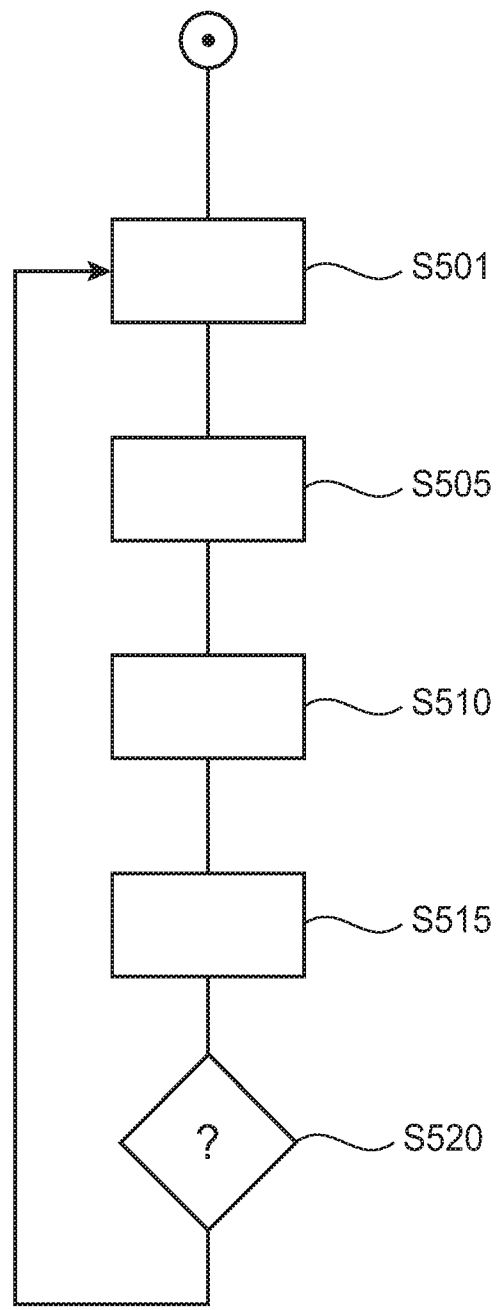
FIG. 5 is a flow chart for a method of visualizing multimodal image material.

In FIG. 5 a flow chart of a method for visualization of image material in a multimodal environment is shown.

At step S501 the X-ray image stream and the ultrasound image stream is received.

At step S505 the two streams are registered onto a common frame of reference for both imaging modalities. In embodiment, the two streams are synchronized prior to registration.

At step S510 a user selected view on the ultrasound volume is received.

In step S515 a fused image for a graphical user interface is generated that affords a 3D view on the US image volume at a certain time instant at the selected view and, concurrently, a perspective view on the X-ray image under perspective distortion, that is, under perspective distortion of the X-ray detector plane.

At step S520 it is determined whether the next frame or volume in the respective stream has been received. If no new X-ray frame or US volume stream has been received, the current view is maintained. If however it is determined at step S520 that a new frame or volume has been received, the previous steps are repeated so as to update in real time the GUI representation on screen.

In one embodiment, step S515 also includes listening for a user request for a new view on the 3D scene, in particular on the ultrasound image and on the X-ray frame XF. If such a request is received the new view is used instead of the current view for the previously mentioned steps. In one embodiment step S515 for generating the graphical user interface also includes listening for a request by the user to designate a point in either the X-ray image or the 3D ultrasound image. If such a request is received the corresponding point in the respective other image is determined and a line of sight is rendered for view connecting the two points.

According to one embodiment step S515 of generating the graphical user interface also includes listening for a magnification or de-magnification request. Said magnification request defines the degree of zooming in or out into the current view.

If such a request is received it is determined whether the magnification or de-magnification would afford a view that accommodates the imager's known SID length, in particular whether the view would afford including the properly scaled distance to the position of the X-ray source XR.

If it is determined that this is the case, a marker is displayed in perspective view representing the X-ray image source position relative to the X-ray image plane. If user so requests, a line of sight is rendered and displayed between two corresponding points with said line extending to the marker of the X-ray source.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for visualizing image material in a multimodal imaging environment, comprising:
   an input port for receiving
   i) an ultrasound image data set acquired of an object by an ultrasound probe and, ii) an X-ray image of the object acquired by an X-ray imager detector in a plane at a projection direction through exposure of the object to radiation emanating from an X-ray imager X-ray source;

a registration unit configured to register the ultrasound image data set in a common frame of reference for both, the X-ray imager and the ultrasound probe; and a graphic user interface (GUI) configured to generate on a screen a graphics display of a 3D scene at a user selectable view that affords, in the common frame of reference for both, the X-ray imager and ultrasound probe, a representation of:

a 3D projection of the ultrasound image data set, and a perspective 3D view on the X-ray image in the plane, the perspective 3D view corresponding to the projection direction and the user selected view, the GUI configured to update the 3D scene according and in response to a user selected second view on the 3D scene, wherein the GUI is configured to generate, responsive to a de-magnification request, a zoomed-out version of the 3D scene so as to accommodate a length of the imager X-ray source to image-receptor distance (SID), with a visual marker indicating a position of the X-ray imager X-ray source relative to the X-ray image in the plane at the user selected view on the ultrasound image data set.

2. The apparatus of claim 1, wherein the GUI is further configured to generate, responsive to a user designating a point of interest in the X-ray image, a line of sight extending from the point of interest across the ultrasound image data set in the selected view on the 3D scene and to the position of the X-ray imager X-ray source, the GUI operative to generate a marker to visually designate a corresponding point on the line and where the line intersects the ultrasound image data in the selected view on the 3D scene.

3. The apparatus of claim 1, wherein the GUI is further configured to generate, responsive to a user designating a point of interest in the ultrasound image data set in the selected view on the 3D scene, a line of sight extending from the point of interest to the position of the X-ray imager X-ray source and extending to a corresponding point in the X-ray image and on the line where the line interests the X-ray image, the GUI operative to generate a marker to visually designate the corresponding point in the X-ray image.

4. The apparatus of claim 1, wherein the ultrasound image is one in a stream of ultrasound image data sets, and wherein the X-ray image is one in a stream of X-ray images, the two streams of X-ray images registered in the common frame of reference, the GUI comprising a tracker to track 1 point of interest over time in the X-ray image stream or in the ultrasound image data set stream, the GUI configured to re-generate a corresponding point in the selected view on the respective ultrasound image data set in the stream or in the respective X-ray image in the stream, and to adapt a line of sight in response to a change in position of the X-ray imager X-ray source or of the ultrasound probe.

5. The apparatus of claim 1, wherein the graphics display is an interactive one and configured to receive the user selected first or second view or the de-magnification request.

6. The apparatus of claim 5, wherein the screen is a touch-screen and wherein the user selection of the selected view and/or of the de-magnification request is by a manual touch or swipe action on the screen.

7. The apparatus of claim 5, wherein the user selection of the selected view and/or of the de-magnification request is by actuating a key on a keyboard or by actuating a pointer tool, the keyboard or the pointer tool communicatively coupled to the apparatus.

8. A method of visualizing image material in a multimodal imaging environment, comprising the steps of:

receiving i) an ultrasound image data set acquired of an object by an ultrasound probe and, ii) an X-ray image of the object acquired by an X-ray imager detector in a plane at a projection direction through exposure of the object to radiation emanating from an X-ray imager X-ray source;

registering the ultrasound image data in a common frame of reference for both, the X-ray imager and the ultrasound probe;

generating on a screen a graphics display of a 3D scene at a user selectable view that affords, in the common frame of reference, a representation of a 3D projection of the ultrasound image data set;

a perspective 3D view on the X-ray image in the detector plane, the perspective 3D view corresponding to the projection direction and the user selected view, the generator configured to update the 3D scene according and in response to a user selected second view on the 3D scene: and responsive to a de-magnification request, generating a zoomed-out version of the 3D scene so as to accommodate a length of the imager's source to image-receptor distance (SID), with a visual marker indicating a position of the X-ray imager X-ray source relative to the X-ray image in the plane at the user selected view on the ultrasound image data set.

9. A non-transitory computer readable medium embodying a program for visualizing image material in a multi-modal imaging environment, the program comprising instructions for performing a plurality of acts, when executed by a processor, is adapted to perform the method of claim 8.

* * * * *